(12) United States Patent
Mueller et al.

(10) Patent No.: US 6,171,502 B1
(45) Date of Patent: Jan. 9, 2001

(54) END PIECE FOR A CHROMATOGRAPHIC COLUMN

(75) Inventors: Hans Daniel Jakob Mueller, Muenster; Axel Delp, Fraenkisch-Crumbach; Hans-Dieter Harders, Darmstadt; Joseph H. Spurk, Bad König; Peter F. Pelz, Mainz, all of (DE)

(73) Assignee: Merck PatentGesellschaft, Darmstadt (DE)

( * ) Notice: Under 35 U.S.C. 154(b), the term of this patent shall be extended for 0 days.

(21) Appl. No.: 09/380,761

(22) PCT Filed: Feb. 25, 1998

(86) PCT No.: PCT/EP98/01052

§ 371 Date: Sep. 13, 1999

§ 102(e) Date: Sep. 13, 1999

(87) PCT Pub. No.: WO98/40734

PCT Pub. Date: Sep. 17, 1998

(30) Foreign Application Priority Data

Mar. 12, 1997 (DE) .............................................. 197 10 117

(51) Int. Cl.⁷ .................................................. B01D 15/08
(52) U.S. Cl. ........................................ 210/656; 210/198.2
(58) Field of Search .................................... 210/635, 656, 210/659, 198.2; 95/82; 96/101

(56) References Cited

U.S. PATENT DOCUMENTS

| 4,354,932 | 10/1982 | McNeil | 210/198.2 |
| 4,422,860 | * 12/1983 | Feinstein | 55/67 |
| 4,966,696 | 10/1990 | Tehrani et al. | 210/198.2 |
| 5,322,626 | * 6/1994 | Frank | 210/656 |

FOREIGN PATENT DOCUMENTS

| 9514220 | 5/1995 | (WO) | 210/198.2 |

* cited by examiner

*Primary Examiner*—Ernest G. Therkorn
(74) *Attorney, Agent, or Firm*—Millen White Zelano & Branigan

(57) ABSTRACT

The present invention provides a column endpiece for a chromatography column. The column endpiece includes a base part, an extension piece for a discharge tube, and a frit. The frit produces a pressure drop per unit length that is at least twice as great as the pressure drop per unit length created in the sorbent packing when the eluent is flowing through.

17 Claims, 4 Drawing Sheets

END PIECE FOR A CHROMATOGRAPHIC COLUMN

REFERENCE TO RELATED APPLICATIONS

This application is a 371 of PCT/EP98/01052 filed Feb. 25, 1998.

The invention relates to an endpiece for chromatography columns, in particular for columns for HPLC.

In the outlet part of chromatography columns, the column endpiece, the cross-sectional area through which flow takes place decreases by several orders of magnitude. This is accompanied by a corresponding change in the flow speed of the column eluate, with additional radial flow components being created. This entails the problem that chromatography bands separated in the column bed are not eluted separately since mixing effects are created by influences at the column outlet. Because of the better separation effects which can be obtained with high performance liquid chromatography (HPLC), the problem is particularly pronounced in HPLC. In preparative HPLC, where column diameters of more than five centimeters are usual, this problem is further exacerbated since the connection lines are particularly small compared with the column diameters.

Known solutions to the problem are presented in standard works for HPLC, for example in "Handbuch der HPLC" [Handbook of HPLC] (ed. K K Unger, 1994, GIT-Verlag). It is customary, for example, to arrange a cylindrical cavity, in which the eluate can flow radially to the column outlet, under a bed support frit. Depending on the position of a volume element in terms of the cross section of the column (i.e. the distance of this element from the column axis), this liquid element will take a different length of time when flowing through the column endpiece. These differences lead to the aforementioned broadening of the eluate bands, and therefore to the deterioration in the separation performance. This deterioration in the separation performance is interpreted by prevalent opinion as being due to the void volume. It is therefore proposed, as a remedy, to use a zero void volume endplate, as can for example be seen from the picture on page 62 of the said handbook. This endplate contains radial indentations in the central region, which do not extend over the entire cross section. The required transverse flow must therefore take place essentially through the dispenser frit; the latter has the form of a planar cylinder. In this embodiment, the described problem of differing propagation times of the volume elements is therefore unresolved. FIG. 4 of EP 0 106 746 schematically represents a column endpiece which has a funnel-shaped outlet. Various chromatography columns are schematically represented on page 105 of J. Chromatogr. Library (Elsevier (1975) volume 3; Liquid Column Chromatography). In this case, there are also column endpieces with a curved profile. However, the problem of flow conditions at the transition between the column and the outlet tube is not discussed in these publications. During the hydrodynamic model calculations which have been described in more detail below, another phenomenon contributing to the band broadening became clear: during these calculations, it was found that the pressure profile is not planar, so that a differing pressure increase occurs in the column endpiece as a function of distance from the column axis. This distorted pressure profile has repercussions on the flow in the column packing.

SUMMARY OF THE INVENTION

The object of the invention is to improve the configuration of endpieces of chromatography columns so that the mixing of boundary regions and concomitant band broadening when the eluate flows through the column outlet are reduced, with the further intention, in particular, of avoiding the repercussions of a distorted, that is to say non-planar, pressure profile on the flow situation on the column packing.

The object is achieved by providing column endpieces whose cross section is configured in such a way that separation surfaces between eluted bands pass in parallel through the column outlet, without becoming excessively distorted. To that end, a column endpiece for a chromatography column is provided which has a cross section that is derived from a cone, the side surface more preferably having a curved contour instead of a straight one. The curved contour is obtained on the basis of hydrodynamic analysis, the equation system resulting in a parabola equation, that is to say a concavely curved contour, or in the equation of an exponential function, that is to say a convexly curved contour, depending on the chosen boundary conditions. It was found that hybrid shapes with sigmoid curvature, which changes over from a concave part into a convex part, are also advantageous. In order to avoid the said repercussions of the distorted pressure profile, pressure decoupling is provided according to the invention between the sorbent bed of the chromatography column and its outlet part. To that end, the discharge frit (2) is configured in such a way that the pressure drop per unit length in the frit is at least twice as great as in the sorbent packing. Measures which make it possible to increase the pressure drop in a frit are known to the person skilled in the art. They include, for example, reducing the porosity of the frit. Although, according to prevalent opinion, the flow resistance in a terminal frit should be kept as small as possible, so that the pressure drop is not increased unnecessarily, the present invention teaches that this pressure drop in the terminal frit should be increased, so that the separation performance of the chromatography column is increased.

When use is made of a terminal frit which causes strong pressure decoupling, a boundary layer is kept substantially undistorted even with a conical contour. In order to obtain sufficient pressure decoupling, the pressure drop per unit length in the frit is at least twice as great as in the sorbent packing.

The invention relates to a column endpiece for a chromatography column, through which eluent flows, comprising a base part (FIGS. 1b, 1c and 3; 1, 1a, 1b), a discharge tube, whose inner profile is denoted by (4) and a frit (2), the base part having an essentially funnel-shaped contour, and, when the eluent is flowing through, the said frit producing a pressure drop per unit length that is at least twice as great as the pressure drop per unit length which is created in the sorbent packing when the eluent is flowing through. In preferred embodiments, the base part has a curved region (FIGS 1b, 1c and 3; 1, 1a, 1b). This curvature may be concave, convex or sigmoidal.

The invention also relates to the use of an endpiece according to the present invention in a chromatography column.

BRIEF DESCRIPTION OF THE DRAWINGS

FIG. 1 represents a longitudinal section through a column endpiece with different variants of terminal profiles (1): Sub

◇: paraboloid terminal profile
▽: exponentially curved terminal profile
○: sigmoidally curved terminal profile
△: conical terminal profile

DESCRIPTION OF THE PREFERRED EMBODIMENTS

In the calculation, the volume of the respective endpiece was set at an equal value in each case.

Figure 1A:
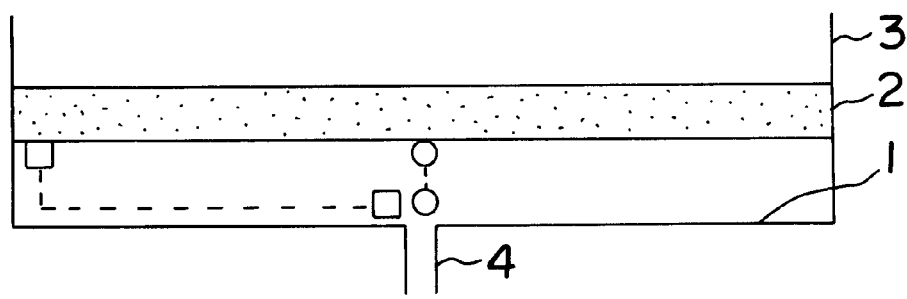
-FIG. 1a represents a longitudinal section through a column endpiece according to the prior art, which has a terminal profile with rectangular profile.

The flow processes in the outlet part of a chromatography column, as known in the prior art, can be described with the aid of FIG. 1a. Two volume elements A (●) and B (■) are represented, as well as their path during the elution. Volume element A is close to the longitudinal axis of the chromatography column, while volume element B is initially at the periphery of the column and does not approach the longitudinal axis of the outlet part in the outlet region until later in the course of the flow. It can be seen immediately that the two volume elements have to travel different distances. Radially adjacent volume elements, which are at the same axial position when flowing into the outlet part, will have different axial positions after having flowed through the outlet part. The effect of this is that volume element B enters the outlet region with a delay, owing to which the concentration transition which originally existed becomes broadened.

This problem is resolved according to the invention in that the outlet part is configured in such a way that parallel planar separation surfaces of the liquid column remain planar and parallel even when they flow through the outlet part. On the basis of this, it has been found that the band broadening can be reduced if, in longitudinal section, the base part has a curved contour (see FIG. 1b or FIG. 1c) instead of the rectilinear/rectangular contour (see FIG. 1a). According to the chosen boundary conditions, a concave (see FIG. 1b) or convex (see FIG. 1c) curvature of the base part results in this case. A sigmoidally curved contour in which the curvature changes from a concave part to a convex part was likewise found to be advantageous. The various boundary conditions will be respectively presented below.

A preferred concave curved shape, which follows a parabolic equation, is disclosed in the sections below. By virtue of the shaping of the base part according to the invention, substances which have been separated along the column are eluted as uniformly as possible when they leave the column, and additional band broadening is substantially avoided. As can already be clearly seen, a rectangular profile is unsuitable for this.

The complete terminal profile is obtained by rotating the curve or, if the curve used is not symmetrical with respect to the y axis, a branch of a curve, about the longitudinal axis of the column. This curve, or this branch of a curve, represents the contour of the terminal profile. As is known, a parabolic equation has the following form:

$$y=a_0+a_1x^1+a_2x^2+a_3x^3+\ldots+a_nx^n$$

Parabolas which describe a symmetrical curve shape, that is to say the constants $a_n$ with odd indices, are equal to zero, are preferred. In particular, the symmetrical second-order parabola with the equation $y=a_0+a_2x^2$ is preferred.

Figure 2A:
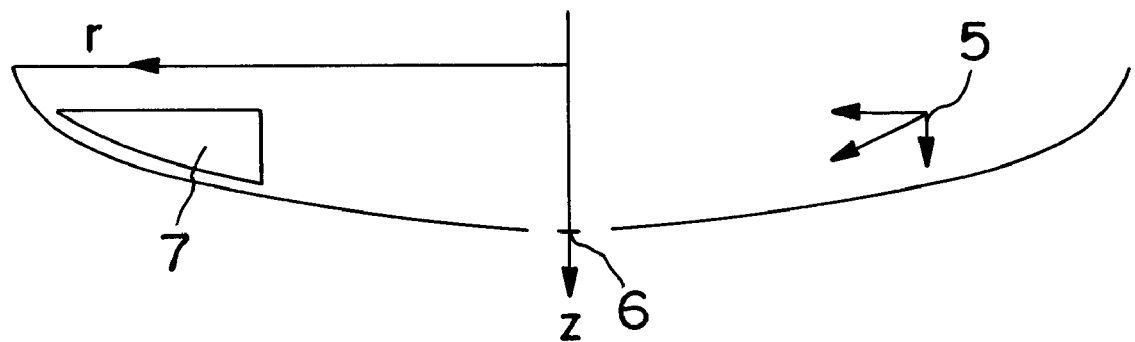
FIG. 2 represents longitudinal sections through column endpieces whose terminal profiles have, according to preferred embodiments, a curved profile. The variables needed for deriving the curvature parameters are also marked. The column endpiece represented in sub-FIG. 2a has a paraboloid contour of the terminal profile.
FIG. 2b represents a longitudinal section through another embodiment of a column endpiece according to the invention, whose terminal profile has an exponentially curved contour. Beside the inner contours of the terminal profiles, the terminal frit (2) of the sorbent bed, the inner profile (3) of the column and the inner profile (4) of the outlet tube are also represented.

If a modelling approach is used for further optimized configuration of the base part, then the time lines on two given cross sections of the outflow should be kept planar and parallel. Other assumptions and boundary conditions which, together with the continuity equation, make it possible to determine an optimum contour curve of the outlet region are compiled in the following section. The designations used are reproduced in FIG. 2a and the other relationships can also be found from this figure. In FIG. 2a: (5) denotes the velocity vectors $U_r$ (in the r direction), $U_z$ (in the z direction) and the resultant U; (6) denotes the height h of the outlet part; the surface (7) denotes the cross section through the control areas A1, A2 and A3, A1 extending in the r direction, A2 in the z direction and A3 along the contour of the outlet part.

Vertical velocity $U_z$ constant, that is to say a planar flow profile should remain planar.

Line sink on the axis. The theoretical representation has no discharge hole per se. The ideal profile and velocity field for a line sink on the axis is presented. If the curve is "flat" enough (that is to say the height is much less than the radius), this is an acceptable simplification.

For given z=const., $$\frac{U_r}{U_z}=\frac{d_r}{d_z},$$

that is to say the liquid flows tangentially to the curve.

Largest radius $r_0$ at z=0.

The curve equation z=f(r) is then looked for and this is obtained by applying the continuity equation to the control volume:

$$\int_{A_1}\int\rho\vec{u}\cdot\vec{n}ds+\int_{A_2}\int\rho\vec{u}\cdot\vec{n}ds+\int_{A_3}\int\rho\vec{u}\cdot\vec{n}ds=0 \text{ with } \rho=konst.$$

Control area A1

$$\int_A \int_1 \vec{u} \cdot \vec{n} ds = \int_r^{r_o} \int_0^{2\pi} -U_z r d\varphi dr = -\pi U_z(r_o^2 - r^2)$$

Control area A2

$$\int_A \int_2 \vec{u} \cdot \vec{n} ds = \int_0^z \int_0^{2\pi} -U_r r d\varphi dz = 2\pi U_z \frac{dr}{dz} rz$$

Control area A3

$$\int_A \int_3 \vec{u} \cdot \vec{n} ds = 0$$

Since A3 extends along the wall.

Substitution in the continuity equation gives:

$$-\pi U_z(r_o^2 - r^2) - 2\pi U_z \frac{dr}{dz} rz = 0 \Rightarrow$$

$$-2rz \frac{dr}{dz} = r_o^2 - r^2 \Rightarrow$$

$$-\int \frac{2r}{r_o^2 - r^2} dr = \int \frac{1}{z} dz \Rightarrow$$

$$\ln(r_o^2 - r^2) = \ln z + c$$

$$z = \tilde{c}(r_o^2 - r^2)$$

The desired curve thus follows a parabolic equation. The constant is determined as follows:

$z(r=r_o)=0$ $z(r=0)=h$; NB for $r \rightarrow 0$, $U_r \rightarrow \infty$

This inconsistency of the model is unimportant for practical embodiments, since the discharge hole lies at the site of the inconsistency. On the other hand, the said boundary conditions and assumptions simplify the mathematical model considerably.

Substituting into the parabolic equation gives $h = \tilde{c} r_o^2$, i.e. $\tilde{c} = \frac{h}{r_o^2}$ This leads to the following for the curve equation:

$$z = h\left(1 - \frac{r^2}{r_o^2}\right)$$

To determine the height h, the following conditions may for example be used:

discharge radius $r_e$=3.5 mm (inner diameter of the discharge tube), largest radius $r_o$=50 mm (inner radius of the separating column), maximum velocity $|\vec{U}|=U_{tube}$ that is to say the velocity of the liquids in the pipeline at the exit of the column. The ratio of the flow velocities in the column tube $U_z(r_0)$ and in the pipeline $U_{tube}$ is obtained in known fashion from the respective cross sections:

Where $$\frac{d_z}{d_r} = -\frac{U_z}{U_r}$$

and $$z = h\left(1 - \frac{r^2}{r_o^2}\right)$$

gives $$-\frac{U_z}{U_r} = \frac{2rh}{r_o^2}$$

The triangle of velocity gives $$U_r = \sqrt{U^2 - U_z^2}$$

which leads to $$h = \frac{r_o^2 U_z}{2r_e \sqrt{U^2 - U_z^2}}$$

For the values above, h≈1.75 mm is found. For the numerical model calculation, h=3 mm was set. The following curve equation resulted:

$$z = 3\left(1 - \frac{r^2}{2500}\right)$$

In this formula, z and r are to be given in mm.

Figure 2B:
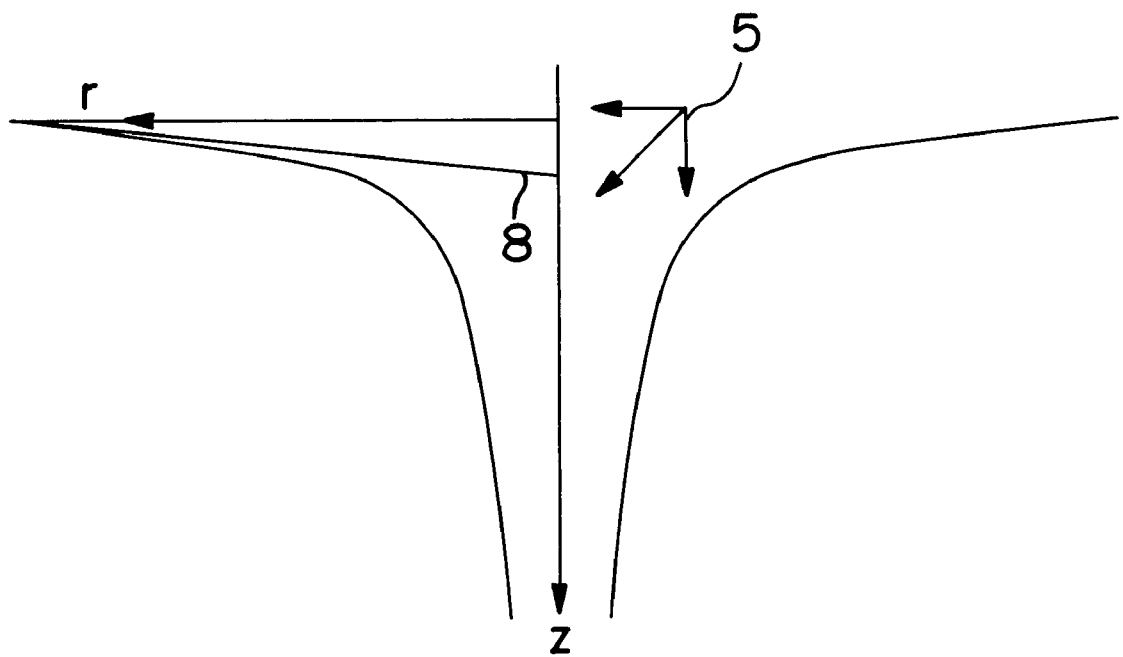

A different, that is to say convex, curve shape which follows the equation of an exponential function is described in the next sections. Using this embodiment according to the invention of the base part, as well, substances separated along the column are eluted as uniformly as possible on leaving the column and additional band broadening is essentially avoided. As will already have become clear, a rectangular profile is unsuitable for this. The explanations below refer to FIG. 2b, in which: (5) denotes the velocity vectors $U_r$ (in the r direction), $U_z$ (in the z direction) and the resultant U; (8) marks the position of the coordinate $\hat{z}$.

The boundary conditions for deriving this curve shape are as follows: In order to obtain a contour according to the invention, it is required that the axial velocity component $u_z$ of the velocity field $$\vec{u}(r,z) = u_z \vec{e}_z + u_z \vec{e}_r$$

is not a function of the radial coordinate r. It is fundamentally required that the mass of a liquid particle remains constant.

One velocity field which satisfies both requirements is:

$$\vec{u}(r, z) = W \exp\left(2\frac{z}{\hat{z}}\right)\left[\vec{e}_z - \frac{r}{\hat{z}} \vec{e}_r\right]$$

The flow lines of the liquid particles are logarithmic curves here. A liquid particle which at time zero was at the position z=0 and r=R follows the path $$r(z) = R * \exp\left(\frac{z}{\hat{z}}\right)$$

This results in a preferred contour of the base part, which follows an exponential curve, $$r(z) = \hat{R} * \exp\left(\frac{z}{\hat{z}}\right)$$

$\hat{R}$ being the column radius.

Figure 4:
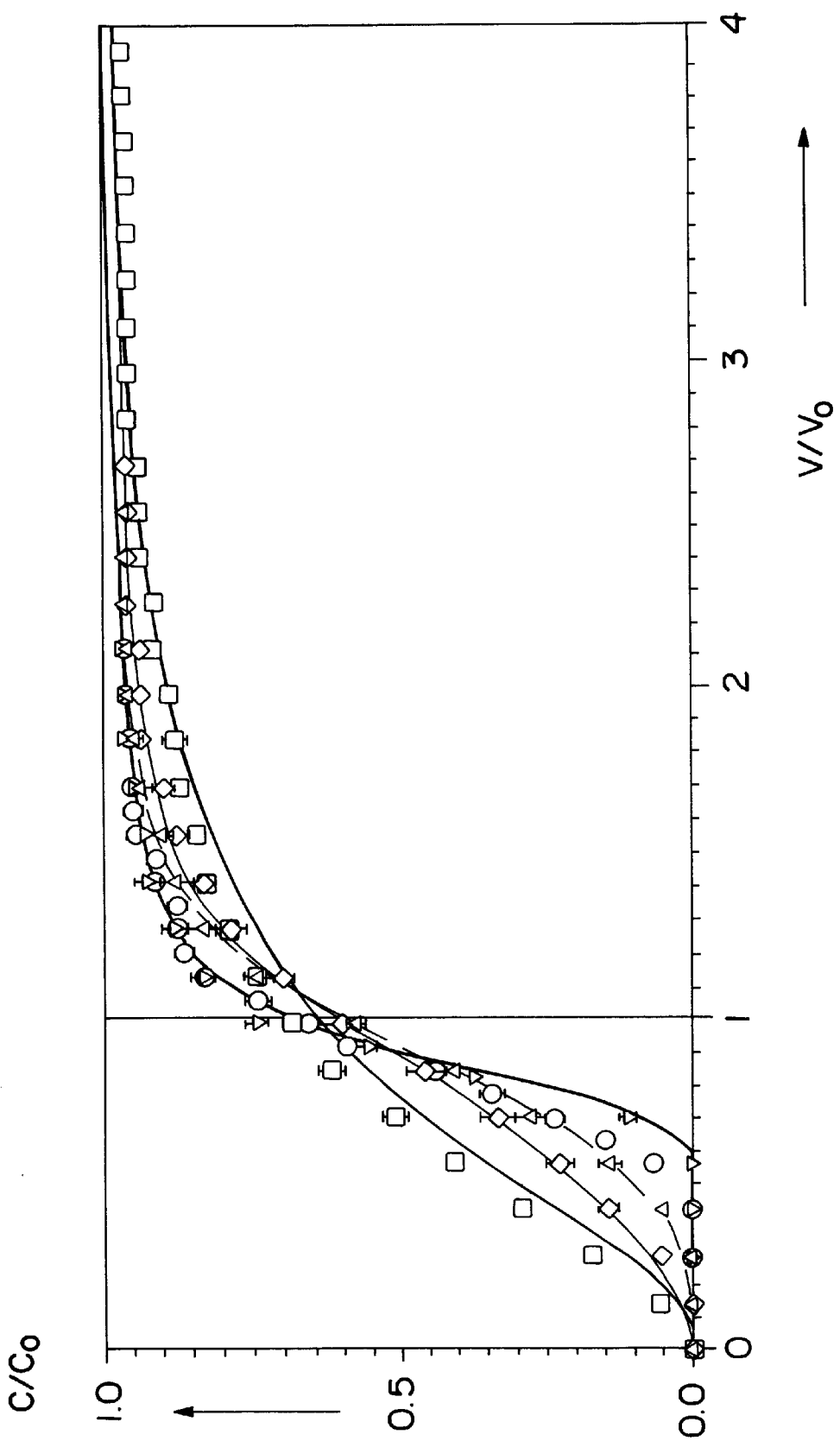
FIG. 4 illustrates concentration changes as occur when a boundary layer passes through a column endpiece. The concentration/maximum concentration ($C/C_0$) ratio is plotted against the eluted volume/volume of the column endpiece ($V/V_0$) ratio. Flow through an endpiece with rectangular terminal profile according to the prior art (symbol ▭) is compared with various embodiments of curved terminal profiles according to the invention.

Since, in any cross section of the base part, all the liquid particles have the same axial velocity component, the front of the chromatography band will remain planar and the break-through curve has the profile represented in FIG. 4.

Figure 3:
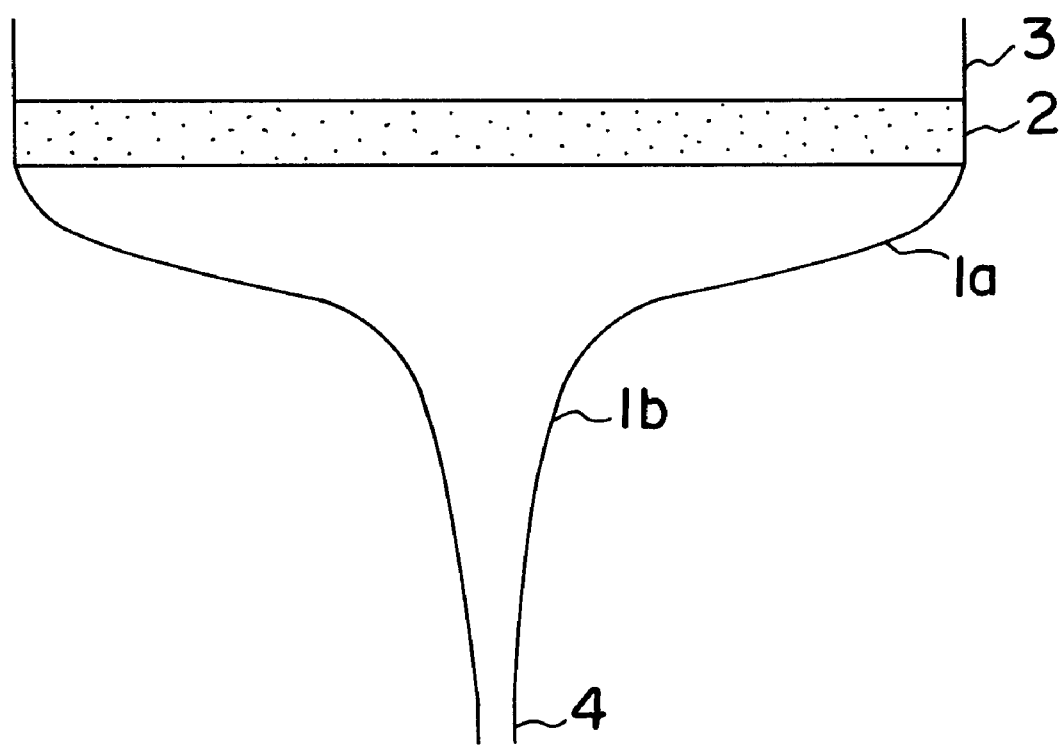
FIG. 3 represents a longitudinal section through a column endpiece whose terminal profile has a sigmoidally curved contour: In the part next to the sorbent bed, the curvature is firstly concave (1a); the curvature then changes into a convex shape (1b).

Another variant of an endpiece according to the invention is represented in FIG. 3: In the upper part, next to the sorbent bed, the curvature is concavely, for example parabolically (1a), curved. The curvature then changes into a convex, for example exponential, curve profile 1b.

By way of example, the contours for the various embodiments of the invention can be represented by the following equations:

a) parabolic, that is to say concave, contour:

$$\frac{R(z)}{a} = \sqrt{1 - \frac{z}{2h}}$$

b) exponential, that is to say convex, contour: c)

$$\frac{R(z)}{a} = \exp\left(-\frac{z}{2h}\right)$$

c) sigmoidal, that is to say concave/convex, contour:

$$\frac{R(z)}{a} = \sqrt{1 - \frac{z}{1,6}} \quad \text{for } 0 \leq \frac{z}{1,6} \leq 1/2$$

respectively $$\frac{R(z)}{a} = \sqrt{\frac{e}{2}} \exp\left(\frac{-z}{1,6}\right) \quad \text{for } \frac{z}{1,6} > 1/2$$

d) Conical contour:

$$\frac{R(z)}{a} = \left(1 - \frac{z}{3h}\right)$$

In the equations above, z is the coordinate along the axis of the column endpiece in the direction of the eluent flow, and r is the coordinate in the radial direction. The variable a denotes the inner diameter of the column, and h denotes the height of the column endpiece (z direction). The funnel radii in proportion to a, i.e. R(z)/a, result from the formulae given above.

As can be seen from the derivations of the curved funnel contours, the said function equations for these funnel contours result from the chosen boundary conditions. Since function equations can, for example, be approximately represented by series expansion, such as the Taylor series, it is obvious to the person skilled in the art that also approximate functions such as these often make it possible to achieve the object of the invention.

In order to avoid the said repercussions of the distorted pressure profile, pressure decoupling is provided according to the invention between the sorbent bed of the chromatography column and its outlet part. To that end, the discharge frit (2) is configured in such a way that the pressure drop per unit length in the frit is at least twice as great as in the sorbent packing. Measures which make it possible to increase the pressure drop in a frit are known to the person skilled in the art. They include, for example, reducing the porosity of the frit. Since the various outlet profiles, as can be established according to the teaching of the present invention, distort the pressure profile in different ways, in some of these embodiments it is possible to keep the pressure decoupling provided according to the invention at a very low level.

Figure 1B:
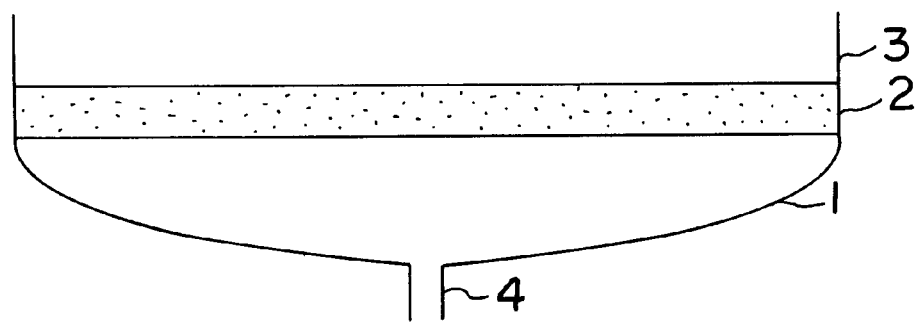
FIG. 1b shows an outlet profile according to the invention with paraboloid, that is to say concavely curved, contour. Sub
Figure 1C:
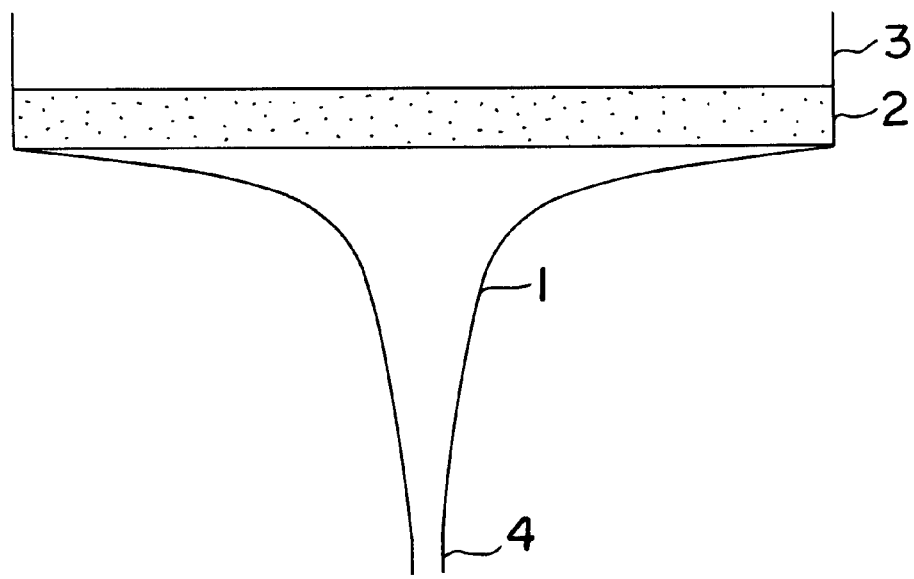
-FIG. 1c shows an outlet profile according to the invention with exponentially curved, that is to say convexly curved, contour. Beside the inner contours of the terminal profiles, the terminal frit (2) of the sorbent bed, the inner profile (3) of the column and the inner profile (4) of the outlet tube are also represented.

If the outflow behaviour of the configurations of the terminal profile which are shown in FIGS. 1a, 1b and 1c, as well as 3, are represented in a model calculation, then the behaviour shown in FIG. 4 is obtained. This can, for example, be calculated using the finite volume program FLUENT. First, the discharge shapes are geometrically mapped using the modelling program preBFC and represented as a physical grid. Next, the constants are established by substituting the corresponding boundary conditions. At the inlet, the axial velocity is set at 600 ml/min. At the outlet, the only stipulation is that the liquid flows out there. The velocity which is set up is calculated by FLUENT. The constants of the liquid are FLUENT's standard settings, i.e. water as liquid:

Density: 1000 kg/m$^3$

Viscosity: $9.0 * 10^{-4}$ kg/ms.

In the subsequent evaluation, the profile shown in FIG. 4 for the different variants of the terminal profile is found for the transit of a boundary layer in which the concentration of an analyte changes from 0 to $c_0$. The following designations are used:

☐ rectangular terminal profile corresponding to the prior art

◇: paraboloid terminal profile

▽: exponentially curved terminal profile

○: sigmoidally curved terminal profile

△: conical terminal profile

In the calculation, the same volume $V_0$ was assumed for all the column endpieces; a further assumption is that the inner radius of the column is large compared with the inner radius of the outlet tube. This condition is satisfied sufficiently if the inner radius of the column is at least ten times greater than the inner radius of the outlet tube; this condition is therefore customarily satisfied for preparative chromatography separating systems.

It is clear that, when using a terminal profile according to the prior art, the boundary layer is distorted considerably, which results in a considerably reduced separating power. In the arrangements according to the invention, this effect is significantly reduced.

Further refinement of the column endpiece (1) according to the invention, can be technically achieved in a variety of ways; these variants are obvious to the person skilled in the art. For example, it is possible to provide a separate endpiece which is connected to the body (2) of the separating column, for example screwed to it. It is also possible to incorporate the endpiece in the separating column and thereby form an integrated part. Furthermore, the base of the endpiece, with its curved terminal profile, may be an integral component of the endpiece. It is, however, also possible to fit a correspondingly shaped insert into a column endpiece with rectangular terminal profile.

According to the invention, the base part may be empty, that is to say it may be without any fitments. There may, however, also be fitments, for example sections which support the frit. The base part may also be filled with porous material. This material may be aggregated, for example sintered or adhesively bonded, to form a shaped article. In this case, if for example the porous material is sintered, a frit is not necessary. The filler material may, however, also consist of loose particles. In one embodiment of the invention, the base part is filled with the same sorbent as is contained in the rest of the column; in this embodiment, the sorbent material is supported by a frit located in the outlet tube.

Even without further details, it may be assumed that a person skilled in the art can employ the above description in its widest scope. The preferred embodiments and examples are therefore to be taken as descriptive disclosure, and not at all as a disclosure implying any limitation.

The entire disclosure of all applications, patents and publications referred to above and below, as well as the corresponding application DE 197 10 117.8, filed on Dec. 3, 1997, are included in this application by reference.

What is claimed is:

1. Column endpiece, for a chromatography column, through which eluent flows, comprising a base part, an extension piece for a discharge tube and a frit, the base part having an essentially funnel-shaped contour, characterized in that, when the eluent is flowing through, the said frit produces a pressure drop per unit length that is at least twice as great as the pressure drop per unit length which is created in the sorbent packing when the eluent is flowing through.

2. Column endpiece according to claim 1, characterized in that the contour is concavely curved.

3. Column endpiece according to claim 1, characterized in that the contour is convexly curved.

4. Column endpiece according to claim 1, characterized in that the contour is curved, and in that the curvature has a concave and a convex part.

5. A chromatographic method comprising flowing an eluent through a chromatography column employing the endpiece of claim 1, such that when the eluent is flowing through, The said frit produces a pressure drop per unit length that is at least twice as great as the pressure drop per unit length which is created in the sorbent packing when the eluent is flowing through.

6. Column endpiece according to claim 1, wherein in any cross-section of the base part all liquid particles have the same axial velocity component.

7. Column endpiece according to claim 1, wherein the contour is parabolic.

8. Column endpiece according to claim 1, wherein the contour is exponential.

9. Column endpiece according to claim 1, wherein the contour is sigmoidal.

10. Column endpiece according to claim 1, wherein the contour is conical.

11. A separating column comprising:

a body; and the column endpiece according to claim 1, wherein the endpiece is screwably connected to the body.

12. A separating column comprising:

the column endpiece according to claim 1, wherein the endpiece is formed integrally with the column.

13. Column endpiece according to claim 1, wherein the base part contains fitments.

14. Column endpiece according to claim 1, wherein the base part contains a porous material.

15. Column endpiece according to claim 14, wherein the porous material is sintered or adhesively bonded.

16. Column endpiece according to claim 14, wherein the porous material comprises loose particles.

17. Column endpiece according to claim 1, wherein the base part contains sorbent material supported by a frit located in the outlet tube.

* * * * *